(12) United States Patent
Yanagisawa

(10) Patent No.: US 8,092,891 B2
(45) Date of Patent: Jan. 10, 2012

(54) BRIDGED CYANINE COMPOUND AND OPTICAL RECORDING MATERIAL USING THE SAME

(75) Inventor: Satoshi Yanagisawa, Tokyo (JP)

(73) Assignee: Adeka Corporation, Tokyo (JP)

( * ) Notice: Subject to any disclaimer, the term of this patent is extended or adjusted under 35 U.S.C. 154(b) by 708 days.

(21) Appl. No.: 12/294,971

(22) PCT Filed: Jul. 10, 2007

(86) PCT No.: PCT/JP2007/063704
§ 371 (c)(1),
(2), (4) Date: Sep. 29, 2008

(87) PCT Pub. No.: WO2008/010433
PCT Pub. Date: Jan. 24, 2008

(65) Prior Publication Data
US 2010/0227108 A1 Sep. 9, 2010

(30) Foreign Application Priority Data
Jul. 21, 2006 (JP) .................................. 2006-199713

(51) Int. Cl.
G11B 7/24 (2006.01)

(52) U.S. Cl. .................. 428/64.8; 428/64.4; 430/270.2; 430/270.21; 548/455; 548/523; 548/524; G9B/7.151

(58) Field of Classification Search ................ 428/64.4, 428/64.8; 430/270.18, 270.2, 270.21; 548/455, 548/524, 523; G9B/7.151
See application file for complete search history.

(56) References Cited

U.S. PATENT DOCUMENTS

| | | | | | |
|---|---|---|---|---|---|
| 2,425,772 | A | * | 8/1947 | Wilson | 540/471 |
| 2,465,774 | A | * | 3/1949 | Wilson | 546/157 |
| 4,680,375 | A | * | 7/1987 | Elmasry | 528/253 |
| 6,761,952 | B1 | * | 7/2004 | Lee et al. | 428/64.1 |
| 7,390,549 | B2 | * | 6/2008 | Wang et al. | 428/64.1 |
| 7,598,360 | B2 | * | 10/2009 | Wang et al. | 534/702 |
| 2006/0142590 | A1 | * | 6/2006 | Wang et al. | 548/416 |
| 2007/0009825 | A1 | * | 1/2007 | Wang et al. | 430/141 |

FOREIGN PATENT DOCUMENTS

| | | |
|---|---|---|
| CN | 1563201 | 1/2005 |
| GB | 804670 | 11/1958 |
| JP | 11-58961 | 3/1999 |
| JP | 2000-231173 | 8/2000 |
| JP | 2001-287465 | 10/2001 |
| JP | 2001-301333 | 10/2001 |
| JP | 2004-339460 | 12/2004 |
| JP | 2006-335662 | 12/2006 |

OTHER PUBLICATIONS

A.K. Chibisov et al.; Photorelaxation Process in Covalently Linked Indocarbocyanine and Thiacarbocyanine Dyes; Journal of Physical Chemistry, 1995, vol. 99, No. 3, pp. 886-893.
Mushkalo, I.L. et al.; 3,3' -Ethylenebis (Benzothiazolium) Salts and their Biscyanine Dyes, Ukrainskii Khimicheskii Zhurnal (Russian Edition), 1977, vol. 43, No. 9, pp. 953-956.
Mushkalo, I.L. et al., 1,1'—Polymethylenebis [carbocyanine] Derivatives of the Indole and Quinoline Series Containing Two Symmetrical Nonconjugated Chromophores, Zhurnal Organicheskoi Khimii, 1987, vol. 23, No. 10, pp. 2212-2216.
Lu,L. et al, Exciton and Charge-Transfer interactions in Nonconjugated Merocyanine Dye Dimers: Novel Solvatochromic Behavior for Tethered Bichromophores and Excimers, Journal of the American Chemical Society, 1999, vol. 121, No. 36, pp. 8146-8156, Dimer-3, Dimer-5, intermediates.
Mushkalo, I.L. et al., Reaction Products of Benzannelated 2,3,3-Trimethyl-3H-Indoles with alpha, omega-dibromoalkanes, and cyanine dyes based on them, Ukrainskii Khimicheskii Zhurnal (Russian Edition) , 1989, vol. 55, No. 3, p. 290-294.
Schmidt, H. et al., ESR in Triplet States of Acridine, Cyanine and Rhodamine dyes and their Aggregates, Semiconductor and Insulators, 1978, vol. 4, No. 3-4, pp. 367-373.
Supplementary European Search Report dated Jun. 8, 2011 in corresponding European Application No. 07 79 0522.
Gromov, S.P. et al., "Reaction of Quinazoline Derivatives With Quaternary Salts of Heterocyclic Bases", Chemistry of Heterocyclic Compounds, Kluwer Academic Publishers-Consultants Bureau, NE, vol. 28, Jan. 1, 1992, pp. 559-566, XP009084185.
Meth-Cohn, O. et al., "The Vilsmeier Formylation of N-(4-Tolyl)pyrrolidine, -piperidine and -perhydroazepine: Further Examples of the 't-Amino Effect'", Tetrahedron Letters, Elsevier, Amsterdam, NL, vol. 37, No. 15, Apr. 8, 1996, pp. 2679-2682, XP004029768.
Moriya, T. et al., "Preparation and Reactions of 3-(Aminomethylene)-3H-indoles", Chemical and Pharmaceutical Bulletin, Pharmaceutical Society of Japan, Tokyo, vol. 28, No. 6, Jan. 1, 1980, pp. 1711-1721, XP008113344.

* cited by examiner

Primary Examiner — Mark Ruthkosky
Assistant Examiner — Gerard Higgins
(74) Attorney, Agent, or Firm — Young & Thompson

(57) ABSTRACT

A cyanine compound is represented by:

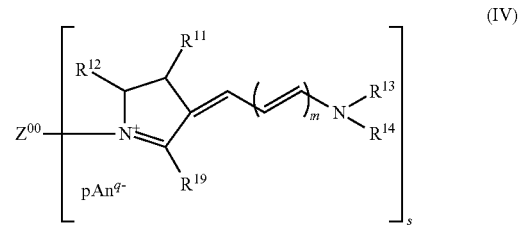

(IV)

wherein, $R^{11}$ and $R^{12}$ each independently represent a hydrogen atom, a hydroxyl group, a halogen atom, a nitro group, a cyano group, an organic group having 1 to 30 carbon atoms, or a group represented by the following general formula (II), (II'), or (III); $R^{13}$ and $R^{14}$ each independently represent a hydrogen atom, an organic group having 1 to 30 carbon atoms, or a substituent represented by the following general formula (III); $R^{11}$ and $R^{12}$ may be connected together to form a ring structure; $R^{19}$ represents a hydrogen atom or an organic group having 1 to 30 carbon atoms; $R^{13}$ and $R^{14}$ may be connected together to form a heterocycle; N—$R^{13}$ may be connected together with a methylene group in a polymethine chain to form a heterocycle; $Z^{00}$ is an organic group having 1 to 10 carbon atoms; m is 0 or 1; s is 2 to 8; $An^{q-}$ represents an anion having a valence of q; q is 1 or 2; and p represents a coefficient for maintaining charge neutrality.

9 Claims, No Drawings

BRIDGED CYANINE COMPOUND AND OPTICAL RECORDING MATERIAL USING THE SAME

TECHNICAL FIELD

The present invention relates to bridged cyanine compounds and metal complexes thereof primarily used for optical recording materials etc., and specifically relates to optical recording materials used in optical recording media for recording information primarily by providing the information as information patterns using lasers etc., and relates more specifically to optical recording materials used in optical recording media capable of high-density optical recording and regeneration using low-energy lasers etc. having wavelengths in the ultraviolet-and-visible region.

BACKGROUND ART

Optical recording media are widely used because of their superior features such as their generally large storage capacity and their capability of non-contact recording/regeneration. In write-once optical discs, such as WORM media, CD-Rs, and DVD±Rs, recording is achieved by condensing a laser beam onto a microscopic area of an optical recording layer and changing the properties thereof, and regeneration is achieved due to the difference in light-reflection amount between the recorded sections and non-recorded sections.

In current optical discs of the above-described type, the wavelengths of semiconductor lasers used for recording/regeneration range from 750 to 830 nm for CD-Rs and from 620 to 690 nm for DVD-Rs. In order to further increase storage capacity, study-and-investigation is being made of optical discs using short-wavelength lasers, such as those using light having wavelengths of 380 to 420 nm as the recording light.

For optical recording media using short-wavelength recording light, various compounds are used in forming the media's optical recording layer. For example, Patent Documents 1 to 3 (listed below) report optical recording materials containing cyanine compounds having specific structures. Those compounds, however, are not always appropriate for optical recording materials used for making optical recording layers in terms of their absorption wavelength properties and durability.

Patent Document 1: Japanese Patent Laid Open JP-A-2001-301333
Patent Document 2: Japanese Patent Laid Open JP-A-2004-339460
Patent Document 3: Japanese Patent Laid Open JP-A-11-58961

DISCLOSURE OF THE INVENTION

Therefore, an object of the present invention is to provide compounds that have superior absorption wavelength properties and light resistance and that are suitable for optical elements used in optical recording materials employing laser beams.

After repeated investigations, Inventor etc. has found that some specifically-structured cyanine compounds bridged at their N-side chains have superior absorption wavelength properties and light resistance, and that the above issue can be addressed by using such compounds.

The present invention has been made based on the above findings and accomplished the objects by providing a cyanine compound represented by the following general formula (I).

[Formula 1]

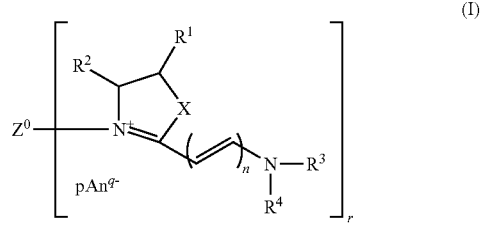

wherein, $R^1$ and $R^2$ each independently represent a hydrogen atom, a hydroxyl group, a halogen atom, a nitro group, a cyano group, an organic group having 1 to 30 carbon atoms, or a group represented by the following general formula (II), (II'), or (III); $R^3$ and $R^4$ each independently represent a hydrogen atom, an organic group having 1 to 30 carbon atoms, or a substituent represented by the following general formula (III); $R^1$ and $R^2$ may be connected together to form a ring structure; $R^3$ and $R^4$ may be connected together to form a heterocycle; $N$—$R^3$ may be connected together with a methylene group in an adjacent polymethine chain to form a heterocycle; X represents an oxygen atom, a sulfur atom, a selenium atom, —$CR^5R^6$—, —NH—, or —$NY^j$—; $R^5$ and $R^6$ each independently represent an organic group having 1 to 30 carbon atoms or a substituent represented by the following general formula (II), (II'), or (III); $R^5$ and $R^6$ may be connected together to form a ring structure; $Y^j$ represents an organic group having 1 to 30 carbon atoms or a group represented by the following general formula (III); $Z^0$ is an organic group having 1 to 10 carbon atoms; n is 1 or 2; r is 2 to 8; $An^{q-}$ represents an anion having a valence of q; q is 1 or 2; and p represents a coefficient for maintaining charge neutrality;

[Formula 2]

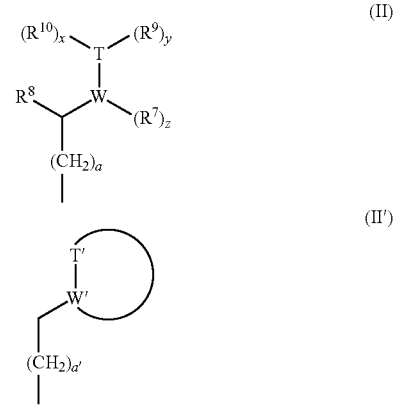

in the general formula (II), a bond between W and T is a double bond, a conjugated double bond, or a triple bond; W represents a carbon atom; T represents a carbon atom or a nitrogen atom; x, y, and z represent 0 or 1; "a" represents a number of 0 to 4; $R^7$ represents a hydrogen atom, a halogen atom, an alkyl group having 1 to 4 carbon atoms that may have a substituent, or an alkoxy group having 1 to 4 carbon atoms that may have a substituent; a methylene group in the alkyl group or the alkoxy group may be substituted by —O— or —CO—; $R^8$, $R^9$, and $R^{10}$ represent a hydrogen atom, a halogen atom, or an alkyl group having 1 to 4 carbon atoms that may have a substituent; a methylene group in the alkyl group may be substituted by —O— or —CO—; and $R^8$ and $R^{10}$ may be bonded to form a ring structure; and, in the general formula (II'): a bond between W' and T' is a double bond or a conjugated double bond; W' represents a carbon atom; T' represents a carbon atom or a nitrogen atom; a' represents a number of 0 to 4; a ring containing W' and T' represents a 5-membered ring that may contain a hetero atom, a 6-membered ring that may contain a hetero atom, a naphthalene ring, a quinoline ring, an isoquinoline ring, an anthracene ring, or an anthraquinone ring; and the ring containing W' and T' may be substituted by a halogen atom, a nitro group, a cyano group, an alkyl group, or an alkoxy group;

[Formula 3]

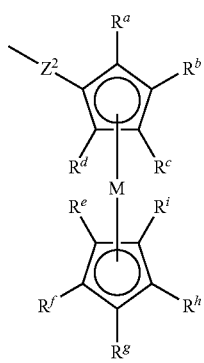

(III)

wherein, $R^a$ to $R^i$ each independently represent a hydrogen atom or an alkyl group having 1 to 4 carbon atoms that may have a substituent; a methylene group in the alkyl group may be substituted by —O— or —CO—; $Z^2$ represents a direct bond or an alkylene group having 1 to 10 carbon atoms that may have a substituent; a methylene group in the alkylene group may be substituted by —O—, —S—, —CO—, —COO—, —OCO—, —SO$_2$—, —NH—, —CONH—, —NHCO—, —N=CH—, or —CH=CH—; and M represents Fe, Co, Ni, Ti, Cu, Zn, Zr, Cr, Mo, Os, Mn, Ru, Sn, Pd, Rh, Pt, or Ir.

In addition, the present invention has accomplished the object by providing a cyanine compound represented by the following general formula (IV).

[Formula 4]

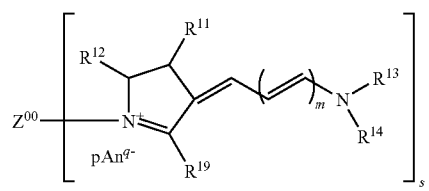

(IV)

wherein, $R^{11}$ and $R^{12}$ each independently represent a hydrogen atom, a hydroxyl group, a halogen atom, a nitro group, a cyano group, an organic group having 1 to 30 carbon atoms, or a group represented by the above general formula (II), (II'), or (III); $R^{13}$ and $R^{14}$ each independently represent a hydrogen atom, an organic group having 1 to 30 carbon atoms, or a substituent represented by the above general formula (III); $R^{11}$ and $R^{12}$ may be connected together to form a ring structure; $R^{19}$ represents a hydrogen atom or an organic group having 1 to 30 carbon atoms; $R^{13}$ and $R^{14}$ may be connected together to form a heterocycle; N—$R^{13}$ may be connected together with a methylene group in a polymethine chain to form a heterocycle; $Z^{00}$ is an organic group having 1 to 10 carbon atoms; m is 0 or 1; s is 2 to 8; and $An^{q-}$, q, and p are as defined in the above general formula (I)).

In addition, the present invention has accomplished the object by providing a cyanine compound represented by the following general formula (V).

[Formula 5]

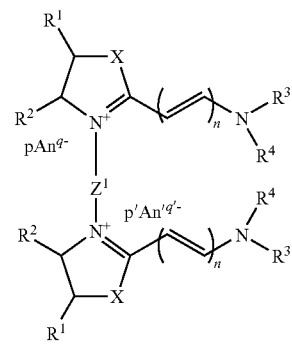

(V)

wherein, $R^1$ and $R^2$ each independently represent a hydrogen atom, a hydroxyl group, a halogen atom, a nitro group, a cyano group, an organic group having 1 to 30 carbon atoms, or a group represented by the above general formula (II), (II'), or (III); $R^3$ and $R^4$ each independently represent a hydrogen atom, an organic group having 1 to 30 carbon atoms, or a substituent represented by the above general formula (III); $R^1$ and $R^2$ may be connected together to form a ring structure; $R^3$ and $R^4$ may be connected together to form a heterocycle; N—$R^3$ may be connected together with a methylene group in an adjacent polymethine chain to form a heterocycle; X represents an oxygen atom, a sulfur atom, a selenium atom, —CR$^5$R$^6$—, —NH—, or —NY$^j$—; $R^5$ and $R^6$ each independently represent an organic group having 1 to 30 carbon atoms or a substituent represented by the above general formula (II), (II'), or (III); $R^5$ and $R^6$ may be connected together to form a ring structure; Y$^j$ represents an organic group having 1 to 30 carbon atoms or a group represented by the above general formula (III); $Z^1$ is a direct bond, an alkylene group having 1 to 10 carbon atoms that may have a substituent, or p-dialkylenebenzene; a methylene group in the alkylene group may be substituted by —O—, —S—, —CO—, —COO—, —OCO—, —SO$_2$—, —NH—, —CONH—, —NHCO—, —N=CH—, or —CH=CH—; n is 1 or 2; $An^{q-}$ represents an anion having a valence of q; $An'^{q'-}$ represents an anion having a valence of q'; q and q' each independently are 1 or 2; and p and p' represent a coefficient for maintaining charge neutrality).

In addition, the present invention has accomplished the object by providing a cyanine compound represented by the following general formula (VI).

[Formula 6]

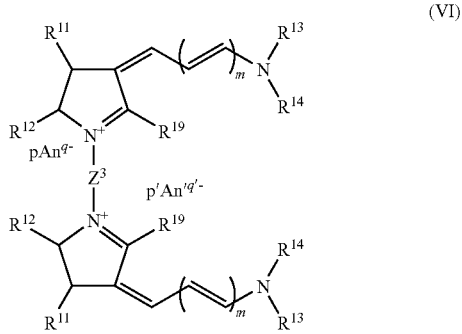

(VI)

wherein, $R^{11}$ and $R^{12}$ each independently represent a hydrogen atom, a hydroxyl group, a halogen atom, a nitro group, a cyano group, an organic group having 1 to 30 carbon atoms, or a group represented by the above general formula (II), (II'), or (III); $R^{13}$ and $R^{14}$ each independently represent a hydrogen atom, an organic group having 1 to 30 carbon atoms, or a substituent represented by the above general formula (III); $R^{11}$ and $R^{12}$ may be connected together to form a ring structure; $R^{19}$ represents a hydrogen atom or an organic group having 1 to 30 carbon atoms; $R^{13}$ and $R^{14}$ may be connected together to form a heterocycle; N—$R^{13}$ may be connected together with a methylene group in a polymethine chain to form a heterocycle; $Z^3$ is a direct bond, an alkylene group having 1 to 10 carbon atoms that may have a substituent, or p-dialkylenebenzene; a methylene group in the alkylene group may be substituted by —O—, —S—, —CO—, —COO—, —OCO—, —SO$_2$—, —NH—, —CONH—, —NHCO—, —N=CH—, or —CH=CH—; m is 0 or 1; and $An^{q-}$, q, p, $An'^{q'-}$, q', and p' are as defined in the above general formula (V).

In addition, the present invention has accomplished the object by providing an optical recording material comprising at least one type of the cyanine compound.

In addition, the present invention has accomplished the object by providing an optical recording medium comprising, on a substrate, an optical recording layer made of the optical recording material.

BEST MODE FOR CARRYING OUT THE INVENTION

Below, cyanine compounds and optical recording materials containing the same of the present invention are described in detail according to their preferred embodiments.

First, the cyanine compound of the present invention represented by the above-described general formula (I) is described.

Examples of halogen atoms represented by $R^1$ and $R^2$ in the above general formula (I) include fluorine, chlorine, bromine, and iodine. Organic groups having 1 to 30 carbon atoms represented by $R^1$, $R^2$, $R^3$, and $R^4$, as well as $R^5$, $R^6$, and $Y^j$ which are the groups in X, in the above general formula (I) are not particularly limited, and examples thereof include: alkyl groups, such as methyl, ethyl, propyl, isopropyl, butyl, sec-butyl, tert-butyl, isobutyl, amyl, isoamyl, tert-amyl, hexyl, cyclohexyl, cyclohexylmethyl, 2-cyclohexylethyl, heptyl, isoheptyl, tert-heptyl, n-octyl, isooctyl, tert-octyl, 2-ethylhexyl, nonyl, isononyl, decyl, dodecyl, tridecyl, tetradecyl, pentadecyl, hexadecyl, heptadecyl, and octadecyl; alkenyl groups, such as vinyl, 1-methylethenyl, 2-methylethenyl, propenyl, butenyl, isobutenyl, pentenyl, hexenyl, heptenyl, octenyl, decenyl, pentadecenyl, and 1-phenylpropene-3-yl; alkylaryl groups, such as phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, and cyclohexylphenyl; arylalkyl groups, such as benzyl, phenethyl, 2-phenylpropane-2-yl, diphenylmethyl, triphenylmethyl, styryl, and cinnamyl; and groups in which the above-mentioned hydrocarbon groups are interrupted by an ether bond or a thioether bond, such as 2-methoxyethyl, 3-methoxypropyl, 4-methoxybutyl, 2-butoxyethyl, methoxyethoxyethyl, methoxyethoxyethoxyethyl, 3-methoxybutyl, 2-phenoxyethyl, 2-methylthioethyl, and 2-phenylthioethyl. Further, these groups may be substituted, for example, by an alkoxy group, an alkenyl group, a nitro group, a cyano group, or a halogen atom.

Examples of ring structures formed by connecting $R^1$ and $R^2$ in the above general formula (I) include: a cyclopropane ring, a cyclobutane ring, a cyclopentane ring, a cyclohexane ring, a benzene ring, a naphthalene ring, an anthracene ring, a piperidine ring, a piperazine ring, a pyrrolidine ring, a morpholine ring, a thiomorpholine ring, a pyridine ring, a pyrazine ring, a pyrimidine ring, a pyridazine ring, a triazine ring, a quinoline ring, an isoquinoline ring, an imidazole ring, an oxazole ring, an imidazolidine ring, a pyrazolidine ring, an isoxazolidine ring, and an isothiazolidine ring. Examples of ring structures formed by connecting $R^5$ and $R^6$, which are groups in X in the above general formula (I), include: a piperidine ring, a piperazine ring, a pyrrolidine ring, a morpholine ring, a thiomorpholine ring, a pyridine ring, a pyrazine ring, a pyrimidine ring, a pyridazine ring, a triazine ring, a quinoline ring, an isoquinoline ring, an imidazole ring, an oxazole ring, an imidazolidine ring, a pyrazolidine ring, an isoxazolidine ring, and an isothiazolidine ring. These rings may be fused with other rings or may be substituted.

Examples of heterocycles formed by $R^3$ and $R^4$ in the above general formula (I), or formed by connecting N—$R^3$ together with a methylene group in the adjacent polymethine chain in the above general formula (I), include: a piperidine ring, a piperazine ring, a pyrrolidine ring, a morpholine ring, a thiomorpholine ring, a pyridine ring, a pyrazine ring, a pyrimidine ring, a pyridazine ring, a triazine ring, a quinoline ring, an isoquinoline ring, an imidazole ring, an oxazole ring, an imidazolidine ring, a pyrazolidine ring, an isoxazolidine ring, and an isothiazolidine ring. These rings may be fused with other rings or may be substituted.

Examples of organic groups having 1 to 10 carbon atoms represented by $Z^0$ in the above general formula (I) include residues of divalent to octavalent alcohols or phenols.

Examples of divalent to octavalent alcohols or phenols include: divalent alcohols, such as ethylene glycol, propylene glycol, 1,4-butylene glycol, neopentyl glycol, 1,6-hexamethylene glycol, and sorbite; divalent phenols, such as catechol, resorcin, and hydroquinone; trivalent alcohols, such as glycerin, trioxyisobutane, 1,2,3-butanetriol, 1,2,3-pentanetriol, 2-methyl-1,2,3-propanetriol, 2-methyl-2,3,4-butanetriol, 2-ethyl-1,2,3-butanetriol, 2,3,4-pentanetriol, 2,3,4-hexanetriol, 4-propyl-3,4,5-heptanetriol, 2,4-dimethyl-2,3,4-pentanetriol, pentamethylglycerin, pentaglycerin, 1,2,4-butanetriol, 1,2,4-pentanetriol, trimethylolethane, and trimethylolpropane; tetravalent alcohols, such as pentaerythritol, 1,2,3,4-pentane tetrol, 2,3,4,5-hexane tetrol, 1,2,4,5-pentane tetrol, 1,3,4,5-hexane tetrol, diglycerol, and sorbitan;

pentavalent alcohols, such as adonitol, arabitol, xylitol, and triglycerin; hexavalent alcohols, such as dipentaerythritol, sorbitol, mannitol, iditol, inositol, dulcitol, talose, and allose; and octavalent alcohols, such as sucrose.

As regards anions represented by $An^{q-}$ in the above general formula (I), examples of monovalent anions include: halide anions, such as chloride, bromide, iodide, and fluoride anions; inorganic anions, such as perchlorate, chlorate, thiocyanate, hexafluorophosphate, hexafluoroantimonate, and tetrafluoroborate anions; organic sulfonate anions, such as benzenesulfonate, toluenesulfonate, trifluoromethanesulfonate, diphenylamine-4-sulfonate, 2-amino-4-methyl-5-chlorobenzenesulfonate, and 2-amino-5-nitrobenzenesulfonate anions; organophosphate anions, such as octyl phosphate, dodecyl phosphate, octadecyl phosphate, phenyl phosphate, nonylphenyl phosphate, and 2,2'-methylenebis(4,6-di-tert-butylphenyl)phosphonate anions; bistrifluoromethylsulfonylimide anion; bisperfluorobutane sulfonyl imide anion; perfluoro-4-ethylcyclohexane sulfonate anion; tetrakis(pentafluorophenyl)borate anion; and tris(fluoroalkylsulfonyl)carbanion. Examples of divalent anions include benzenedisulfonate and naphthalenedisulfonate anions. If necessary, it is also possible to use, for example, quencher anions serving to de-excite (quench) excited active molecules or metallocene compound anions of, for example, ferrocene or ruthenocene having an anionic group, such as a carboxyl group, a phosphonic group, or a sulfonic group, on the cyclopentadienyl ring.

Further, p and p' are selected so that the electric charge of the entire molecule becomes neutral.

Examples of the above-mentioned quencher anions include compounds represented by the following general formula (A) or (B) or the following formula (C), or anions disclosed, for example, in Japanese Patent Laid Open JP-A-60-234892, Japanese Patent Laid Open JP-A-5-43814, Japanese Patent Laid Open JP-A-5-305770, Japanese Patent Laid Open JP-A-6-239028, Japanese Patent Laid Open JP-A-9-309886, Japanese Patent Laid Open JP-A-9-323478, Japanese Patent Laid Open JP-A-10-45767, Japanese Patent Laid Open JP-A-11-208118, Japanese Patent Laid Open JP-A-2000-168237, Japanese Patent Laid Open JP-A-2002-201373, Japanese Patent Laid Open JP-A-2002-206061, Japanese Patent Laid Open JP-A-2005-297407, Japanese Examined Patent JP-B-7-96334, or International Publication WO 98/29257.

[Formula 7]

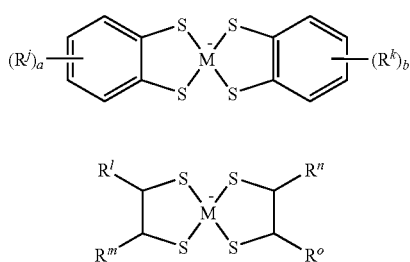

wherein, M represents Fe, Co, Ni, Ti, Cu, Zn, Zr, Cr, Mo, Os, Mn, Ru, Sn, Pd, Rh, Pt, or Ir; $R^j$ and $R^k$ represent a halogen atom, an alkyl group having 1 to 8 carbon atoms, an aryl group having 6 to 30 carbon atoms, or a $-SO_2$-G group; G represents an alkyl group, an aryl group that may be substituted by a halogen atom, a dialkylamino group, a diarylamino group, a piperidino group, or a morpholino group; "a" and "b" each independently represent a number of 0 to 4; and $R^l$, $R^m$, $R^n$, and $R^o$ each independently represent an alkyl group, an alkylphenyl group, an alkoxyphenyl group, or a halogenated phenyl group.

[Formula 8]

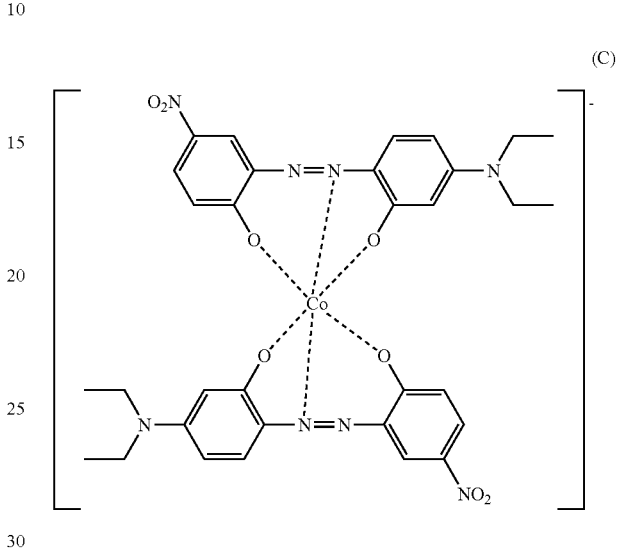

Examples of alkyl groups having 1 to 4 carbon atoms represented by $R^7$, $R^8$, $R^9$, and $R^{10}$ in the above general formula (II) include methyl, ethyl, propyl, isopropyl, butyl, sec-butyl, tert-butyl, and isobutyl. Examples of groups whose methylene group in the alkyl group is substituted by —O— include methoxy, ethoxy, propyloxy, isopropyloxy, methoxymethyl, ethoxymethyl, and 2-methoxyethyl. Examples of groups whose methylene group in the alkyl group is substituted by —CO— include acetyl, 1-carbonylethyl, acetylmethyl, 1-carbonylpropyl, 2-oxobutyl, 2-acetylethyl, and 1-carbonylisopropyl. Alkoxy groups having 1 to 4 carbon atoms represented by $R^7$ in the above general formula (II) include groups having an ether group added to one of the above exemplified alkyl groups having 1 to 4 carbon atoms.

Examples of halogen atoms represented by $R^7$, $R^8$, $R^9$, and $R^{10}$ in the above general formula (II) include the atoms given as examples of the halogen atoms represented by $R^1$ and $R^2$ in the above general formula (I).

Examples of ring structures formed by connecting $R^8$ and $R^{10}$ in the above general formula (II) include structures given as examples of the ring structures formed by connecting $R^5$ and $R^6$, which are the groups existing in X in the above general formula (I).

In the above general formula (II'), examples of 5-membered rings that may contain a hetero atom include a cyclopentene ring, a cyclopentadiene ring, an imidazole ring, a thiazole ring, a pyrazole ring, an oxazole ring, an isoxazole ring, a thiophene ring, a furan ring, and a pyrrole ring, and examples of 6-membered rings that may contain a hetero atom include a benzene ring, a pyridine ring, a piperazine ring, a piperidine ring, a morpholine ring, a pyrazine ring, a pyrone ring, and a pyrrolidine ring.

Examples of alkyl groups having 1 to 4 carbon atoms represented by $R^a$ to $R^j$ in the above general formula (III) include the groups given as examples in the above general formula (II).

Examples of alkylene groups having 1 to 10 carbon atoms represented by $Z^2$ in the above general formula (III) include methylene, ethylene, propylene, methylethylene, butylene, 1-methylpropylene, 2-methylpropylene, 1,2-dimethylpropylene, 1,3-dimethylpropylene, 1-methylbutylene, 2-methylbutylene, 3-methylbutylene, 4-methylbutylene, 2,4-dimethylbutylene, 1,3-dimethylbutylene, pentylene, hexylene, heptylene, octylene, ethane-1,1-diyl, and propane-2,2-diyl. Examples of groups whose methylene group in the alkylene group is substituted by —O—, —S—, —CO—, —COO—, —OCO—, —SO$_2$—, —NH—, —CONH—, —NHCO—, —N=CH—, or —CH=CH— include methyleneoxy, ethyleneoxy, oxymethylene, thiomethylene, carbonylmethylene, carbonyloxymethylene, methylenecarbonyloxy, sulfonylmethylene, aminomethylene, acetylamino, ethylenecarboxyamide, ethaneimidoyl, ethenylene, and propenylene.

Next, the cyanine compound of the present invention represented by the above general formula (IV) is described.

Examples of halogen atoms represented by $R^{11}$ and $R^{12}$ in the above general formula (IV) include the atoms given as examples of the halogen atoms represented by $R^1$ and $R^2$ in the above general formula (I). Examples of organic groups having 1 to 30 carbon atoms represented by $R^{11}$, $R^{12}$, $R^{13}$, $R^{14}$, and $R^{19}$ in the above general formula (IV) include the groups given as examples of the organic groups having 1 to 30 carbon atoms represented by $R^1$, $R^2$, $R^3$, and $R^4$ in the above general formula (I).

Examples of ring structures formed by connecting $R^{11}$ and $R^{12}$ in the above general formula (IV) include the structures given as examples of the ring structures formed by connecting $R^1$ and $R^2$ in the above general formula (I).

Examples of heterocycles formed by $R^{13}$ and $R^{14}$ in the above general formula (IV), or formed by connecting N—$R^{13}$ together with a methylene group in the adjacent polymethine chain in the above general formula (IV), include the ones given as examples of the heterocycles formed by $R^3$ and $R^4$ in the above general formula (I), or formed by connecting N—$R^3$ together with a methylene group in the adjacent polymethine chain in the above general formula (I).

Examples of organic groups having 1 to 10 carbon atoms represented by $Z^{00}$ in the above general formula (IV) include the groups given as examples of the organic groups having 1 to 10 carbon atoms represented by $Z^0$ in the above general formula (I).

An example of a cyanine compound represented by the above general formula (I) includes the cyanine compound represented by the above general formula (V), which corresponds to the case where r=2 in the formula (I).

Similarly, an example of a cyanine compound represented by the above general formula (IV) includes the cyanine compound represented by the above general formula (VI), which corresponds to the case where s=2 in the formula (IV).

Examples of methods for producing these compounds include methods for producing the cyanine compounds represented by the above general formulas (V) and (VI), which are described further below.

Further, examples of cyanine compounds represented by the above general formula (I) and corresponding to cases where r=3 to 8 in the formula, as well as cyanine compounds represented by the above general formula (IV) and corresponding to cases where s=3 to 8 in the formula, include the following compounds A and B.

[Formula 9]

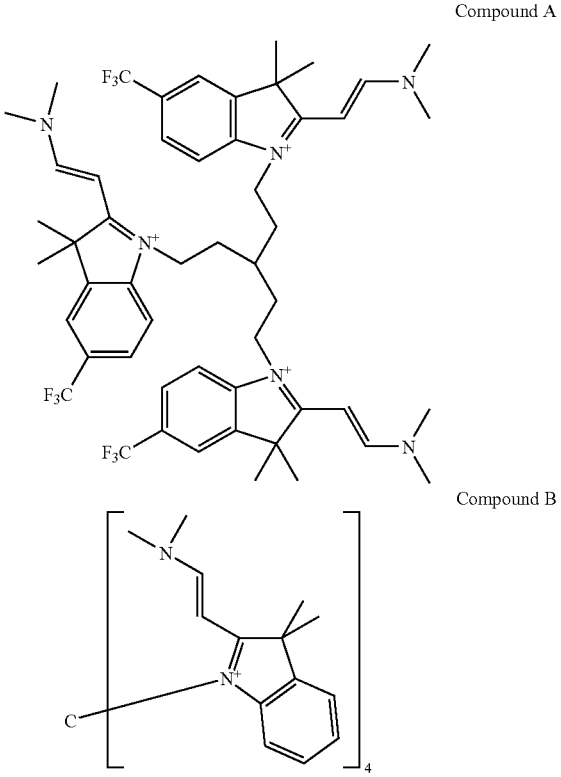

Compound A

Compound B

There are no particular limitations to the methods for producing the cyanine compounds represented by the above general formula (I) and corresponding to cases where r=3 to 8 in the formula, as well as the cyanine compounds represented by the above general formula (IV) and corresponding to cases where s=3 to 8 in the formula. For example, the hydroxyl group(s) of a trivalent to octavalent alcohol or phenol may be substituted with a halogen atom, and the methods for producing the cyanine compounds represented by the above general formulas (V) and (VI), which are described below, may be employed as the methods for producing the above compounds.

Next, the cyanine compounds of the present invention represented by the above general formulas (V) and (VI) are described.

Examples of alkylene groups having 1 to 10 carbon atoms represented by $Z^1$ in the above general formula (V), as well as alkylene groups having 1 to 10 carbon atoms which are groups existing in p-dialkylenebenzene represented by $Z^1$, include the examples given in the explanation on the above general formula (III).

Examples of anions represented by $An'^{q'-}$ in the above general formula (V) include the ones given as examples of the anions represented by $An^{q-}$ in the above general formula (I).

Examples of alkylene groups having 1 to 10 carbon atoms represented by $Z^3$ in the above general formula (VI), as well as alkylene groups having 1 to 10 carbon atoms which are groups existing in p-dialkylenebenzene represented by $Z^3$, include the examples given in the explanation on the above general formula (III).

Among the cyanine compounds represented by the above general formula (V), the compound represented by the following general formula (VII) is preferable in terms that the manufacturing cost is low and that it is particularly suitable for forming optical recording layers in optical recording media for short-wavelength lasers having absorption wavelength properties of 380 to 420 nm.

Further, among the cyanine compounds represented by the above general formula (VI), the compound represented by the following general formula (VIII) is preferable for the same reasons as above.

[Formula 10]

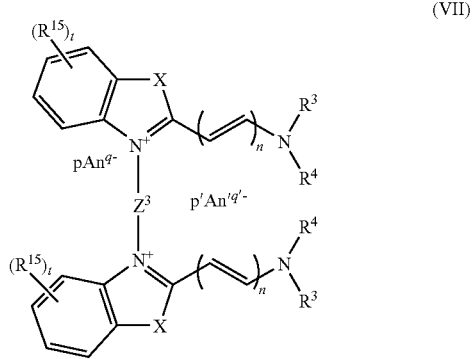

(VII)

wherein, $R^{15}$ represents a hydrogen atom, an organic group having 1 to 30 carbon atoms, a nitro group, an amino group, a halogen atom, a cyano group, or a heterocycle group having 2 to 20 carbon atoms; t is a number of 1 to 4; and $Z^1$, $R^3$, $R^4$, X, n, $An^{q-}$, q, p, $An'^{q'-}$, q', and p' are as defined in the above general formula (V).

[Formula 11]

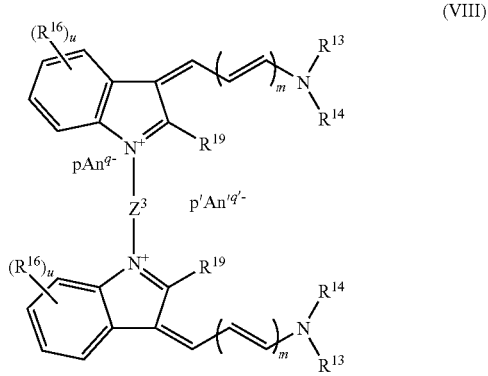

(VIII)

wherein, $R^{16}$ represents a hydrogen atom, an organic group having 1 to 30 carbon atoms, a nitro group, an amino group, a halogen atom, a cyano group, or a heterocycle group having 2 to 20 carbon atoms; u is a number of 1 to 5; $An^{q-}$, q, p, $An'^{q'-}$, and p' are as defined in the above general formula (V); and $Z^3$, $R^{13}$, $R^{14}$, $R^{19}$, and m are as defined in the above general formula (VI).

Examples of amino groups represented by $R^{15}$ in the above general formula (VII) include amino, ethylamino, dimethylamino, diethylamino, butylamino, cyclopentylamino, 2-ethylhexylamino, dodecylamino, anilino, chlorophenylamino, toluidino, anisidino, N-methyl-anilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino, N,N-dimethylaminocarbonylamino, N,N-diethylaminocarbonylamino, morpholinocarbonylamino, methoxycarbonylamino, ethoxycarbonylamino, t-butoxycarbonylamino, n-octadecyloxycarbonylamino, N-methyl-methoxycarbonylamino, phenoxycarbonylamino, sulfamoylamino, N,N-dimethylaminosulfonylamino, methylsulfonylamino, butylsulfonylamino, phenylsulfonylamino, trimethylammonio, and triethylammonio. Examples of heterocycle groups having 2 to 20 carbon atoms represented by $R^{15}$ in the above general formula (VII) include pyridyl, pyrimidyl, pyridazyl, piperazyl, piperidyl, pyranyl, pyrazolyl, triazyl, pyrrolidyl, quinolyl, isoquinolyl, imidazolyl, benzoimidazolyl, triazolyl, furyl, furanyl, benzofuranyl, thienyl, thiophenyl, benzothiophenyl, thiadiazolyl, thiazolyl, benzothiazolyl, oxazolyl, benzooxazolyl, isothiazolyl, isooxazolyl, indolyl, julolidyl, morpholinyl, thiomorpholinyl, 2-pyrrolidinone-1-yl, 2-piperidone-1-yl, 2,4-dioxyimidazolidine-3-yl, and 2,4-dioxyoxazolidine-3-yl.

Examples of amino groups represented by $R^{16}$ in the above general formula (VIII) include the groups given as examples of the amino groups represented by $R^{15}$ in the above general formula (VII). Examples of heterocycle groups having 2 to 20 carbon atoms represented by $R^{16}$ in the above general formula (VIII) include the groups given as examples of the heterocycle groups having 2 to 20 carbon atoms represented by $R^{15}$ the above general formula (VII).

Any of the following groups may have a substituent: the organic groups having 1 to 30 carbon atoms represented by $R^1$, $R^2$, $R^3$, and $R^4$ in the above general formula (V), $R^{11}$, $R^{12}$, $R^{13}$, and $R^{14}$ in the above general formula (VI), $R^{15}$ in the above general formula (VII), $R^{16}$ in the above general formula (VIII), and $R^5$, $R^6$, and $Y^j$ which are groups existing in X; the ring structures formed by connecting either $R^1$ and $R^2$ in the above general formula (V), $R^8$ and $R^{10}$ in the above general formula (II), $R^5$ and $R^6$ which are groups existing in X, or $R^{11}$ and $R^{12}$ in the above general formula (VI); the heterocycles formed by connecting either $R^3$ and $R^4$ in the above general formula (V), $R^{13}$ and $R^{14}$ in the above general formula (VI), or N—$R^3$ in the above general formula (V) or N—$R^{13}$ in the above general formula (VI) together with a methylene group in the adjacent polymethine chain; the alkylene groups having 1 to 10 carbon atoms represented by $Z^1$ in the above general formulae (V) and (VII), $Z^2$ in the above general formula (III), and $Z^3$ in the above general formulae (VI) and (VIII), or existing in p-dialkylenebenzene which is a group in $Z^1$ in the above general formulae (V) and (VII) and a group in $Z^3$ in the above general formulae (VI) and (VIII); the amino groups represented by $R^{15}$ in the above general formula (VII) and $R^{16}$ in the above general formula (VIII); the alkyl groups having 1 to 4 carbon atoms represented by $R^7$, $R^8$, $R^9$, and $R^{10}$ in the above general formula (II) and $R^a$ to $R^i$ in the above general formula (III); and the alkoxy groups having 1 to 4 carbon atoms by $R^7$, $R^8$, $R^9$, and $R^{10}$ in the above general formula (II) and $R^a$ to $R^i$ in the above general formula (III). Examples of the substituents are listed below. Note that in cases where any of $R^1$ to $R^{16}$, Y, and $Z^1$ to $Z^3$ are groups containing carbon atoms, such as the above-described organic group having 1 to 30 carbon atoms, and those groups have a substituent—among the following substituents—that contains carbon atoms, then the number of carbon atoms of the entire group $R^1$ to $R^{16}$ etc. including the substituent should be within the defined range.

Examples of the above-mentioned substituents include: alkyl groups, such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl, 2-ethylhexyl, nonyl, isononyl, and decyl; alkoxy groups, such as methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, nonyloxy, and decyloxy; alkylthio groups, such as methylthio, ethylthio, propylthio, isopropylthio, butylthio, sec-butylthio, tert-butylthio, isobutylthio, amylthio, isoamylthio, tert-amylthio, hexylthio, cyclohexylthio, heptylthio, isoheptylthio, tert-heptylthio, n-octylthio, isooctylthio, tert-octylthio, and 2-ethylhexylthio; alkenyl groups, such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicosenyl, and tricosenyl; arylalkyl groups, such as benzyl, phenethyl, diphenylmethyl, triphenylmethyl, styryl, and cinnamyl; aryl groups, such as phenyl and naphthyl; aryloxy groups, such as phenoxy and naphthyloxy; arylthio groups, such as phenylthio and naphthylthio; heterocycle groups, such as pyridyl, pyrimidyl, pyridazyl, piperidyl, pyranyl, pyrazolyl, triazyl, pyrrolyl, quinolyl, isoquinolyl, imidazolyl, benzoimidazolyl, triazolyl, furyl, furanyl, benzofuranyl, thienyl, thiophenyl, benzothiophenyl, thiadiazolyl, thiazolyl, benzothiazolyl, oxazolyl, benzooxazolyl, isothiazolyl, isooxazolyl, indolyl, 2-pyrrolidinone-1-yl, 2-piperidone-1-yl, 2,4-dioxyimidazolidine-3-yl, and 2,4-dioxyoxazolidine-3-yl; halogen atoms, such as fluorine, chlorine, bromine, and iodine; acyl groups, such as acetyl, 2-chloroacetyl, propionyl, octanoyl, acryloyl, methacryloyl, phenylcarbonyl(benzoyl), phthaloyl, 4-trifluoromethylbenzoyl, pivaloyl, salicyloyl, oxaloyl, stearoyl, methoxycarbonyl, ethoxycarbonyl, t-butoxycarbonyl, n-octadecyloxycarbonyl, and carbamoyl; acyloxy groups, such as acetyloxy and benzoyloxy; substituted amino groups, such as amino, ethylamino, dimethylamino, diethylamino, butylamino, cyclopentylamino, 2-ethylhexylamino, dodecylamino, anilino, chlorophenylamino, toluidino, anisidino, N-methyl-anilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino, N,N-dimethylaminocarbonylamino, N,N-diethylaminocarbonylamino, morpholinocarbonylamino, methoxycarbonylamino, ethoxycarbonylamino, t-butoxycarbonylamino, n-octadecyloxycarbonylamino, N-methyl-methoxycarbonylamino, phenoxycarbonylamino, sulfamoylamino, N,N-dimethylaminosulfonylamino, methylsulfonylamino, butylsulfonylamino, and phenylsulfonylamino; sulfone amide groups; sulfonyl groups; carboxyl groups; cyano groups; sulfo groups; hydroxyl groups; nitro groups; mercapto groups; imide groups; carbamoyl groups; and sulfone amide groups. These groups may further be substituted. Further, carboxyl groups and sulfo groups may be in the form of salts.

Specific examples of cyanine compounds represented by the above general formulae (V), (VI), (VII), and (VIII) of the present invention include the following compounds Nos. 1 to 15. Note that the following examples are shown as cations without the anions. In the compounds of the present invention, the double bond may have a resonance structure.

[Formula 12]

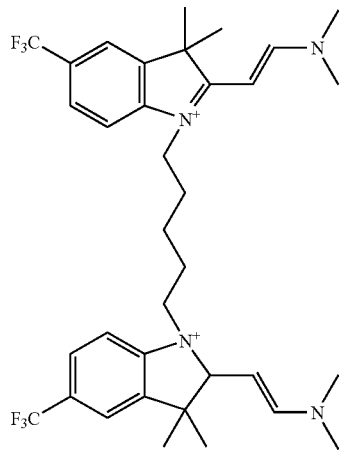

Compound No. 1

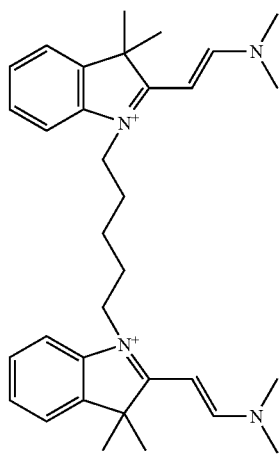

Compound No. 2

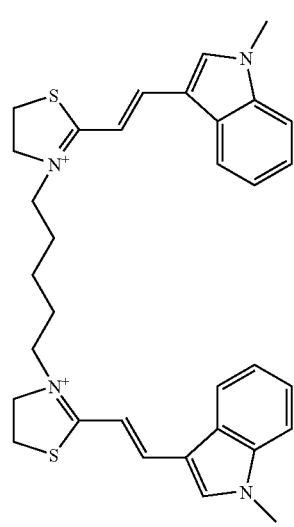

Compound No. 3

Compound No. 4
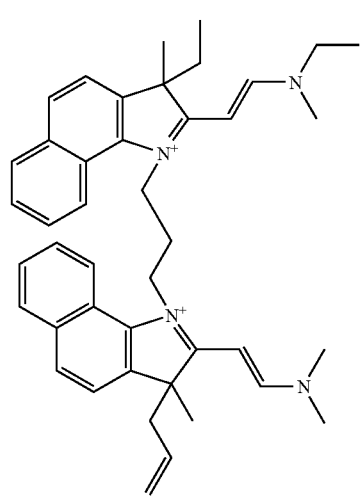
Compound No. 5
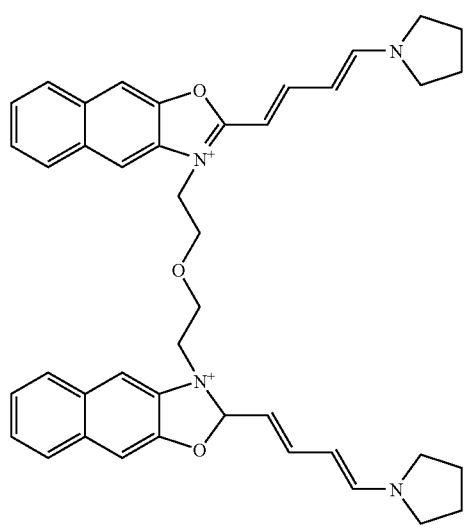
Compound No. 6
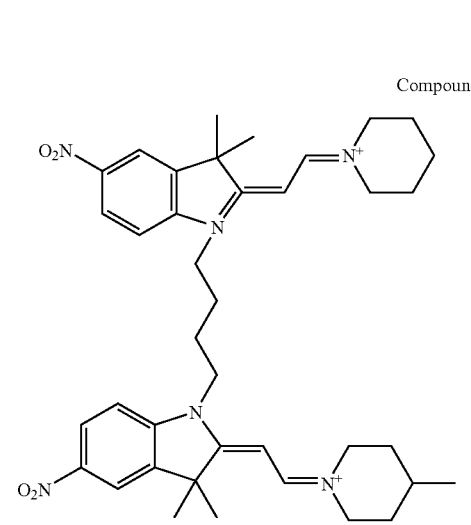
Compound No. 7
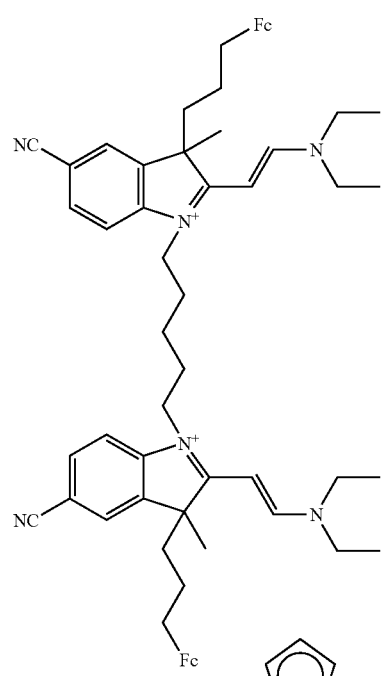
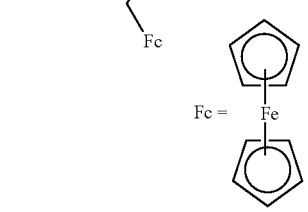
Compound No. 8

Compound No. 9
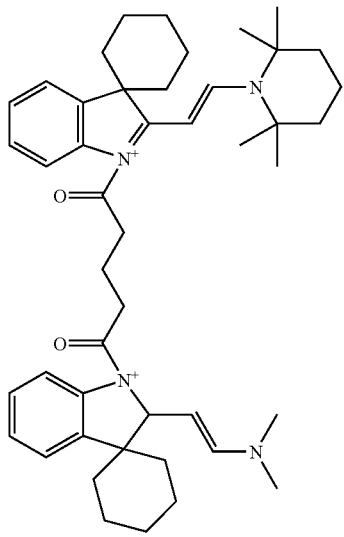
Compound No. 12
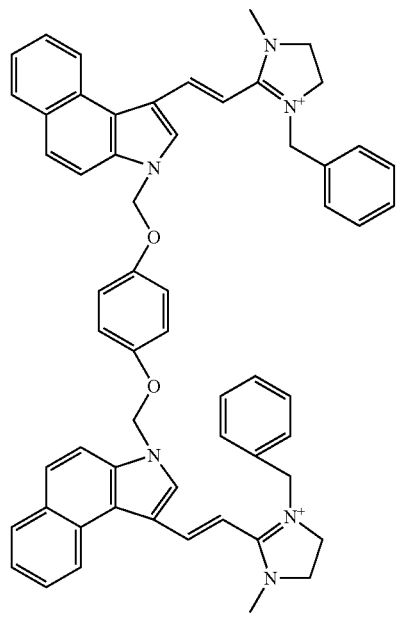
[Formula 13]
Compound No. 10
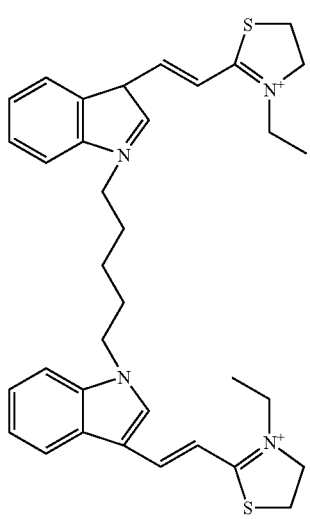
Compound No. 13
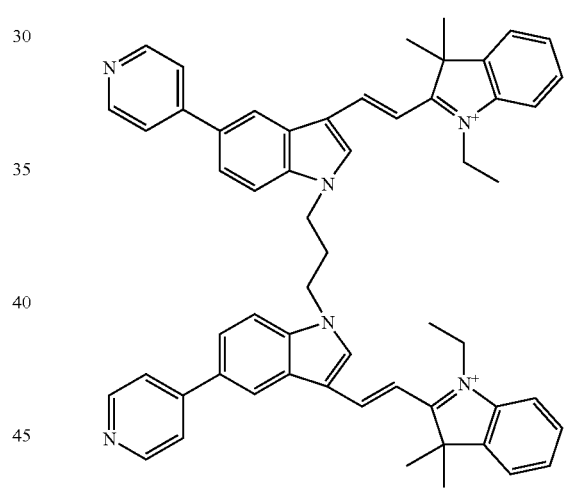
Compound No. 11
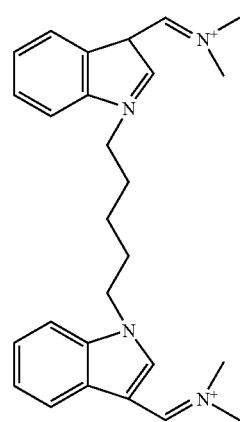
Compound No. 14
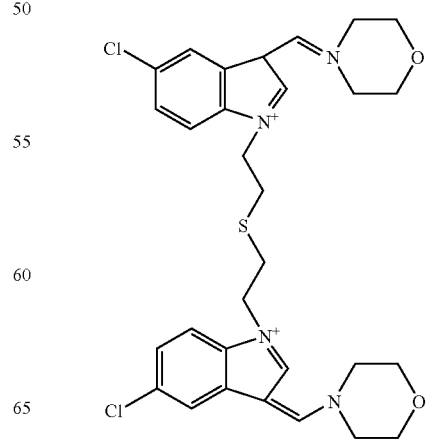

Compound No. 15

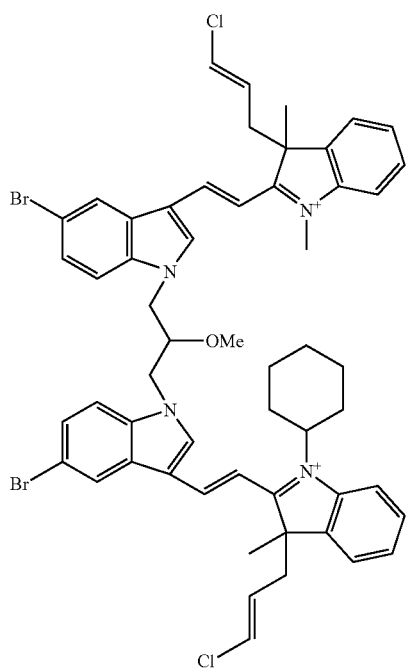

The cyanine compound represented by the above general formula (V) is not particularly limited by the production method thereof, and can be obtained through methods employing generally known reactions. For example, a compound having n=1 can be synthesized by reacting an alkyl dihalide with 2 equivalents of an indolenine compound and then undergoing the Vilsmeier reaction, as in the equation shown in the following [Formula 14]. A compound having n=2 can also be synthesized according to the route shown in the following [Formula 14].

[Formula 14]

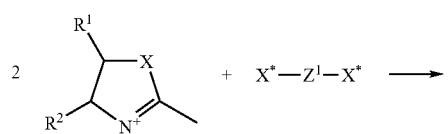

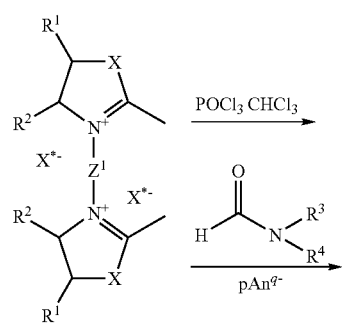

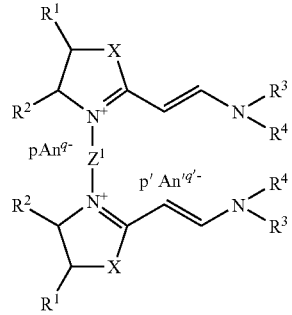

In the formula, $R^1$, $R^2$, $R^3$, $R^4$, X, n, $Z^1$, $An^{q-}$, q, p, $An'^{q'-}$, q', and p' are the same as those in the above general formula (V), and X* is a halogen atom.

The cyanine compound represented by the above general formula (VI) is not particularly limited by the production method thereof, and can be obtained through methods employing generally known reactions. For example, a compound having m=0 can be synthesized by reacting an alkyl dihalide with 2 equivalents of an indole compound and then undergoing the Vilsmeier reaction, as in the equation shown in the following [Formula 15]. A compound having m=1 can also be synthesized according to the route shown in the following [Formula 15].

[Formula 15]

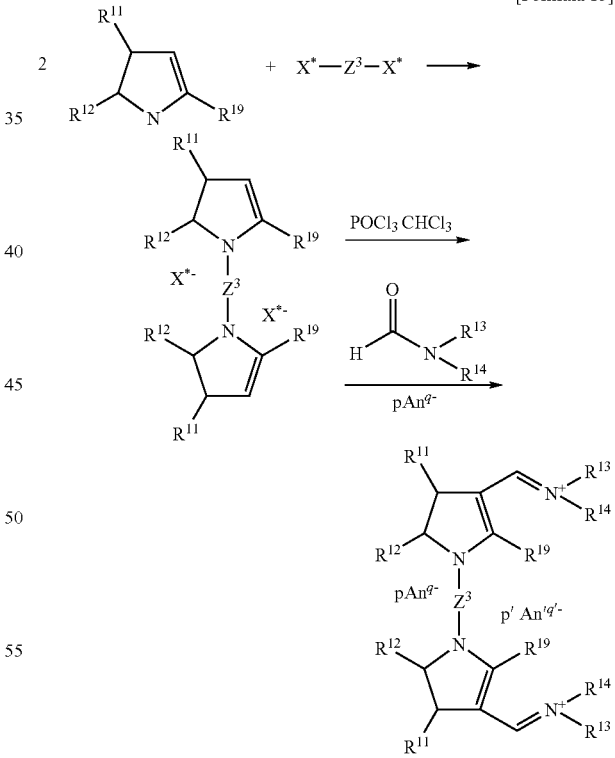

In the formula, $An^{q-}$, q, p, $An'^{q'-}$, q', and p' are the same as those in the above general formula (V), $R^{11}$, $R^{12}$, $R^{13}$, $R^{14}$, $R^{19}$, m, and $Z^3$ are the same as those in the above general formula (VI), and X* is the same as that in the above [Formula 14].

As seen in [Table 5], the cyanine compounds represented by the above general formulae (I) and (IV) of the present invention exhibited a high absorbance residual rate even after being held in high temperature for 400 hours.

The cyanine compounds of the present invention described above are suitable for optical elements for light within the range of 450 nm to 1100 nm, and more preferably for light within the range of 480 to 620 nm. An "optical element" is an element that exerts its functions by absorbing light of a specific type, and specific examples thereof include light absorbers, optical recording agents, and photosensitizers. For example, optical recording agents are used for optical recording layers in optical recording media such as DVD±Rs, and light absorbers are used in optical filters for image displaying devices, such as liquid crystal displays (LCDs), plasma display panels (PDPs), electroluminescent displays (ELDs), cathode-ray tube displays (CRTs), vacuum fluorescent displays, and field emission displays, or for analyzers, semiconductor-device manufacturing, astronomical observations, or optical communications.

The following describes an optical recording material of the present invention that contains the cyanine compound of the present invention and that is used for an optical recording layer in an optical recording medium having the optical recording layer formed on a substrate. The cyanine compounds of the present invention represented by the above general formulae (I) and (IV) to (VIII) are also useful for optical recording materials used for optical recording layers in optical recording media for recording information by providing the information as thermal information patterns with lasers etc., and the compounds are particularly suitable for optical recording materials used for optical recording layers in optical recording media, such as DVD-Rs, DVD+Rs, and blue-laser discs. Note that the optical recording material of the present invention is a material used for making an optical recording layer, and is a mixture of the cyanine compound of the present invention represented by either one of the above general formulae (I) and (IV) to (VIII) and an organic solvent and/or various other compounds described below.

There is no particular limitation to the method of making an optical recording layer of an optical recording medium using the optical recording material of the present invention containing the cyanine compound represented by either one of the above general formulae (I) and (IV) to (VIII). Generally, an optical recording material solution is prepared by dissolving the cyanine compound of the present invention and, if necessary, various later-described compounds, into an organic solvent, e.g.: lower alcohols, such as methanol and ethanol; ether alcohols, such as methyl cellosolve, ethyl cellosolve, butyl cellosolve, and butyl diglycol; ketones, such as acetone, methylethyl ketone, methylisobutyl ketone, cyclohexanone, and diacetone alcohol; esters, such as ethyl acetate, butyl acetate, and methoxyethyl acetate; acrylate esters, such as ethyl acrylate and butyl acrylate; fluorinated alcohols, such as 2,2,3,3-tetrafluoropropanol; hydrocarbons, such as benzene, toluene, and xylene; or chlorinated hydrocarbons, such as methylene dichloride, dichloroethane, and chloroform. Then, the wet coating method is employed, in which the optical recording material is coated onto a substrate by, for example, spin coating, spraying, or dipping. Vapor deposition or sputtering may also be employed. In cases of using the above organic solvent, it is preferable to adjust the usage amount thereof so that the content of the cyanine compound represented by either one of the above general formulae (I) and (IV) to (VIII) with respect to the optical recording material of the present invention is within 0.1% to 10% by mass.

The optical recording layer is formed as a thin film, and generally, its thickness is suitably 0.001 to 10 μm, and preferably 0.01 to 5 μm.

In the optical recording material of the present invention, the content of the cyanine compound represented by either one of the above general formulae (I) and (IV) to (VIII) is preferably 10% to 100% by mass with respect to the amount of solid matter contained in the optical recording material of the invention. It is preferable that the optical recording layer is made so as to contain 50% to 100% by mass of the cyanine compound represented by either one of the above general formulae (I) and (IV) to (VIII) in the optical recording layer. To form an optical recording layer having such a compound content, it is more preferable that the optical recording material of the present invention contains 50% to 100% by mass of the cyanine compound represented by either one of the above general formulae (I) and (IV) to (VIII) relative to the amount of solid matter contained in the optical recording material of the invention.

The "solid matter" contained in the optical recording material of the present invention refers to the components excluding non-solid components, such as organic solvents, from the optical recording material. The content of the solid matter is preferably 0.01% to 100% by mass, and more preferably 0.1% to 10% by mass, with respect to the optical recording material.

In addition to the cyanine compound of the present invention, the optical recording material of the present invention may contain, as necessary, such compounds as the following: compounds generally used in optical recording layers, such as azo-based compounds, phthalocyanine-based compounds, oxonol-based compounds, squarylium-based compounds, indole compounds, styryl-based compounds, porphin-based compounds, azulenium-based compounds, croconic methine-based compounds, pyrylium-based compounds, thiopyrylium-based compounds, triarylmethane-based compounds, diphenylmethane-based compounds, tetrahydrocholine-based compounds, indophenol-based compounds, anthraquinone-based compounds, naphthoquinone-based compounds, xanthene-based compounds, thiazine-based compounds, acridine-based compounds, oxazine-based compounds, spiropyran-based compounds, fluorene-based compounds, and rhodamine-based compounds; resins, such as polyethylene, polyester, polystyrene, and polycarbonate; surfactants; antistatic agents; slip additives; fire retardants; radical scavengers such as hindered amine; pit-forming accelerators such as ferrocene derivatives; dispersing agents; antioxidants; cross-linking agents; and light-resistance imparting agents. The optical recording material of the present invention may further contain, for example, aromatic nitroso compounds, aminium compounds, iminium compounds, bisiminium compounds, or transition metal chelate compounds as quenchers for singlet oxygen etc. In the optical recording material of the present invention, these various compounds are used in an amount ranging from 0% to 50% by mass with respect to the amount of solid matter contained in the optical recording material of the invention.

The material for the substrate on which the optical recording layer is provided is not particularly limited, as long as it is substantially transparent to the light for writing (recording) and for reading (regeneration). For example, resins, such as polymethyl methacrylate, polyethylene terephthalate, and polycarbonate, or glass may be used. A substrate having any shape can be used, such as a tape, drum, belt, or disk, depending on how it is going to be used.

Further, a reflective film may be formed on the optical recording layer by vapor deposition or sputtering using gold, silver, aluminum, copper, etc. A protective layer may also be formed using acrylic resin, UV curing resin, etc.

EXAMPLES

The following describes the present invention in further detail through examples and evaluation examples. The present invention, however, is not limited in any way by the following examples etc.

The following examples 1 to 3 describe production of the cyanine compound represented by the above general formula (I). The following examples 4 and 5 describe production of the cyanine compound represented by the above general formula (IV). The following examples 6 to 10 describe examples of optical recording materials and optical recording media of the present invention using the respective cyanine compounds of the present invention obtained in the examples 1 to 5. Comparative examples 1 and 2 describe examples of optical recording materials and optical recording media using compounds having structures different from the cyanine compounds of the present invention. The following evaluation example 1 evaluates the light resistance of the cyanine compounds of the present invention obtained in the examples 1 and 2 and a comparative compound 1. The following evaluation example 2 evaluates the thermal stability of the optical recording media obtained in the examples 6 and 7 and a comparative optical recording medium obtained in the comparative example 1. The following evaluation example 3 evaluates the optical recording media obtained in the examples 6 and 7 and the comparative optical recording media obtained in the comparative examples 1 and 2 in terms of recording/regeneration suitability using a short-wavelength laser.

Examples 1 to 3

Synthesis of Quencher Anion Salts of Compounds Nos. 1 and 2 and $PF_6$ Salt of Compound No. 2

<Step 1> Synthesis of Intermediates 1 to 3

20 mmol of an indolenine compound, 20 mmol of diiodopentane, and 30 ml of dimethylformamide were mixed and stirred for 4 hours at 120° C. The mixture was cooled to room temperature, filtered, and dried, to obtain intermediates 1 to 3.

<Step 2> Synthesis of $PF_6$ Salts of Compounds Nos. 1 and 2

7 ml of an aldehyde derivative and 44 ml of chloroform were mixed, 30 mmol of phosphorus oxychloride was dropped therein on ice, and the mixture was stirred for 1 hour on ice. Then, 10 mmol each of the intermediates obtained in Step 1 were added on ice, and the mixture was stirred and heated under reflux for 3 hours. After cooling to room temperature, 179 mmol of $KPF_6$ and 650 ml of water were added, the mixture was stirred for 1 hour, and the precipitation was filtered and separated. After washing with methanol, the precipitation was dried, to obtain the target compounds, i.e., $PF_6$ salts of the compounds Nos. 1 and 2.

<Step 3> Synthesis of Quencher Anion Salts of Compounds Nos. 1 and 2

Each of 3.0 mmol of the compounds obtained in Step 2 was dissolved into 12 ml of acetone. A solution having 6.0 mmol of a triethylamine salt of the anion shown in formula [C] dissolved into 120 ml of acetone was dropped into the above mixture, 28 ml of acetone was further added, and the mixture was heated under reflux for 3 hours. After cooling to room temperature, the resultant was dropped into 1800 ml of water, and the mixture was stirred for 6 hours at room temperature. The precipitated solid was filtered and separated, washed with methanol, and dried, to obtain the target compounds, i.e., the respective quencher anion salts of the compounds Nos. 1 and 2.

Examples 4 and 5

Synthesis of $PF_6$ Salts of Compounds Nos. 10 and 11

<Step 1> Synthesis of Intermediates 4 and 5

20 mmol of an indole compound, 20 mmol of diiodopentane, and 30 ml of dimethylformamide were mixed and stirred for 4 hours at 120° C. The mixture was cooled to room temperature, filtered, and dried, to obtain intermediates 4 and 5.

<Step 2> Synthesis of $PF_6$ Salt of Compound No. 11

12 ml of an aldehyde derivative and 74 ml of chloroform were mixed, 37 mmol of phosphorus oxychloride was dropped therein on ice, and the mixture was stirred for 1 hour on ice. Then, 12 mmol of the intermediate 5 obtained in Step 1 was added on ice, and the mixture was stirred and heated under reflux for 3 hours. After cooling to room temperature, 163 mmol of $KPF_6$ and 500 ml of water were added, the mixture was stirred for 1 hour, and the precipitation was filtered and separated. After washing with methanol, the precipitation was dried, to obtain the target compound, i.e., a $PF_6$ salt of the compound No. 11.

<Step 3> Synthesis of $PF_6$ Salt of Compound No. 10

4.8 mmol of the intermediate 4 obtained in Step 1, 9.6 mmol of N-alkylthiazoline, and 20 ml of pyridine were mixed, and the mixture was stirred for 3.5 hours at 100° C. The mixture was cooled to room temperature, the solvent was distilled away, the solute was recrystallized in acetone, and the obtained compound was filtered and dried, to obtain the target compound, i.e., a $PF_6$ salt of the compound No. 10.

The yield and analysis results of the compounds obtained in the examples 1 to 5 are shown in Tables 1 to 3. Note that in Table 1, the "decomposition point" is the temperature at which the mass starts to decrease in differential thermal analysis at a temperature-rising rate of 10° C./min.

TABLE 1

| | Compound | Yield (%) | lmax (nm) | e ($\times 10^5$) | Decomposition point (° C.) |
|---|---|---|---|---|---|
| Example 1 | Quencher anion salt of Compound No. 1 | 91 | 549.5 | 1.20 | 297 |
| Example 2 | Quencher anion salt of Compound No. 2 | 79 | 548.0 | 1.20 | 293 |
| Example 3 | $PF_6$ salt of Compound No. 2 | 93 | 368.0 | 0.76 | 324 |
| Example 4 | $PF_6$ salt of Compound No. 10 | 59 | 426.0 | 0.82 | 276 |
| Example 5 | $PF_6$ salt of Compound No. 11 | 85 | 345.0 | 0.33 | 314 |

TABLE 2

| | Compound | IR absorption spectrum (cm$^{-1}$) |
|---|---|---|
| Example 1 | Quencher anion salt of Compound No. 1 | 1613, 1577, 1476, 1389, 1323, 1285, 1263, 1169, 1141, 1123 |
| Example 2 | Quencher anion salt of Compound No. 2 | 2975, 1611, 1476, 1320, 1285, 1265 |
| Example 3 | PF$_6$ salt of Compound No. 2 | 2934, 1631, 1556, 1412, 1271, 1197, 1117, 841 |
| Example 4 | PF$_6$ salt of Compound No. 10 | 2929, 1597, 1570, 1514, 1400, 1340, 1240, 1150, 843 |
| Example 5 | PF$_6$ salt of Compound No. 11 | 2948, 1651, 1525, 1407, 1243, 1111, 840, 758 |

TABLE 3

| | Compound | $^1$H-NMR (DMSO-d6) |
|---|---|---|
| Example 1 | Quencher anion salt of Compound No. 1 | 9.00 (d, 4H, J = 2.9 Hz), 8.37 (d, 2H, J = 12.2 Hz), 8.00 (s, 2H), 7.85 (dd, 4H, J = 9.0, 2.7 Hz), 7.70-7.55 (m, 6H), 7.38 (d, 2H, J = 8.3 Hz), 6.65 (d, 4H, J = 9.0 Hz), 6.35 (dd, 4H, J = 9.5, 2.4 Hz), 5.74 (d, 4H, J = 2.4 Hz), 5.61 (d, 2H, J = 12.2 Hz), 4.06 (t, 4H, J = 6.3 Hz), 3.49 (s, 6H), 3.38-3.21 (m, 16H), 3.18 (s, 6H), 1.85-1.62 (m, 4H), 1.58 (s, 12H), 1.34-1.25 (m, 2H), 1.01 (t, 24H, J = 6.8 Hz) |
| Example 2 | Quencher anion salt of Compound No. 2 | 9.00 (d, 4H, J = 2.9 Hz), 8.25 (d, 2H, J = 12.4 Hz), 7.85 (dd, 4H, J = 9.0, 2.9 Hz), 7.64 (d, 4H, J = 9.3 Hz), 7.55 (d, 2H, J = 7.3 Hz), 7.35-7.19 (m, 6H), 6.55 (d, 4H, J = 9.0 Hz), 6.35 (dd, 4H, J = 9.5, 2.7 Hz), 5.74 (d, 4H, J = 2.7 Hz), 5.51 (d, 2H, J = 12.4 Hz), 4.06 (t, 4H, J = 6.6 Hz), 3.45 (s, 6H), 3.29 (q, 16H, J = 7.1 Hz), 3.10 (s, 6H), 1.75-1.64 (m, 4H), 1.55 (s, 12H), 1.35-1.25 (m, 2H), 1.01 (t, 24H, J = 7.1 Hz) |
| Example 3 | PF$_6$ salt of Compound No. 2 | 8.27 (d, 2H, J = 12.4 Hz), 7.57 (d, 2H, J = 7.3 Hz), 7.38-7.18 (m, 6H), 5.53 (d, 2H, J = 12.4 Hz), 4.11 (t, 4H, J = 6.6 Hz), 3.48 (s, 6H), 3.12 (s, 6H), 1.78-1.65 (m, 4H), 1.55 (s, 12H), 1.39-1.26 (m, 2H) |
| Example 4 | PF$_6$ salt of Compound No. 10 | 8.50 (s, 2H), 8.13 (dd, 2H, J = 6.6, 2.0 Hz), 8.05 (d, 2H, J = 15.1 Hz), 7.67 (dd, 2H, J = 6.6, 2.0 Hz), 7.40-7.25 (m, 4H), 7.07 (d, 2H, J = 15.4 Hz), 4.48 (t, 4H, J = 8.3 Hz), 4.28 (t, 4H, J = 6.8 Hz), 4.03 (q, 4H, J = 7.1 Hz), 3.64 (t, 4H, J = 8.3 Hz), 1.94-1.78 (m, 4H), 1.38-1.24 (m, 2H), 1.31 (t, 6H, J = 7.1 Hz) |
| Example 5 | PF$_6$ salt of Compound No. 11 | 9.19 (s, 2H), 8.71 (s, 2H), 8.12-8.05 (m, 2H), 7.80-7.69 (m, 2H), 7.58-7.35 (m, 4H), 4.39 (t, 4H, J = 6.8 Hz), 3.76 (s, 6H), 3.55 (s, 6H), 1.99-1.79 (m, 4H), 1.37-1.21 (m, 2H) |

Examples 6 to 10

Manufacturing of Optical Recording Materials and Optical Recording Media

Each of the compounds obtained in the above examples 1 to 5 was dissolved into a 2,2,3,3-tetrafluoropropanol solution so that the compound concentration becomes 1.0% by mass, and the respective optical recording materials of examples 6 to 10 were obtained in the form of 2,2,3,3-tetrafluoropropanol solutions. The respective optical recording media Nos. 1 to 5 of the examples 6 to 10 were obtained by coating each of the above-described optical recording materials through spin-coating, to thereby form an optical recording layer 100 nm thick, on a 12-cm-dia. polycarbonate disk substrate having a primary-coating layer (0.01 μm) formed by coating a titanium chelate compound ("T-50" available from Nippon Soda Co., Ltd.) and then causing hydrolysis.

Comparative Examples 1 and 2

Optical recording materials of comparative examples 1 and 2 were prepared in the same way as the examples 6 to 10, except that the following comparative compounds Nos. 1 and 2 were respectively used instead of the compounds obtained in the examples 1 to 5. Comparative optical recording media Nos. 6 and 7 of the comparative examples 1 and 2 were obtained using those optical recording materials.

[Formula 16]

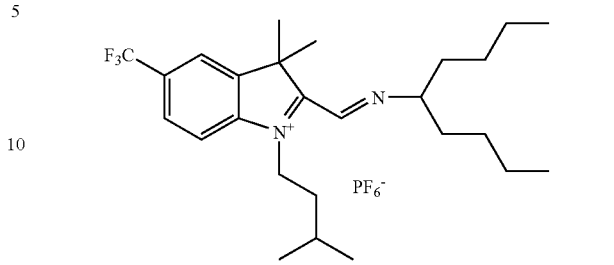

Comparative compound No. 1

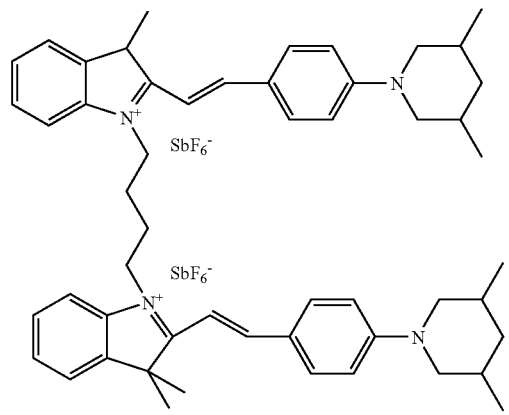

Comparative compound No. 2

Evaluation Examples 1-1 and 1-2 and Comparative Evaluation Example 1-1

Evaluation of Light Resistance of Cyanine Compounds Represented by General Formulae (I) and (IV)

Evaluation was made on the light resistance of the quencher anion salts of the compounds Nos. 1 and 2 obtained in the examples 1 and 2 and the comparative compound 1.

First, each compound of the present invention was dissolved into 2,2,3,3-tetrafluoropropanol so that the concentration becomes 1% by mass, to prepare a 2,2,3,3-tetrafluoropropanol solution. Test pieces were prepared by respectively coating the obtained solutions onto a 20×20 mm polycarbonate plate through spin-coating at 2000 rpm for 60 seconds. Evaluation was made by irradiating 55,000 lux of light onto each test piece for 24 hours and 300 hours, and thereafter measuring the absorbance residual rate at λmax of the UV absorption spectrum before irradiation. The results are shown in [Table 4].

TABLE 4

| | | Absorbance residual rate (%) | |
|---|---|---|---|
| | Compound | After 24 hours | After 300 hours |
| Evaluation example 1-1 | Quencher anion salt of Compound No. 1 | 95.4 | 90.2 |
| Evaluation example 1-2 | Quencher anion salt of Compound No. 2 | 96.4 | 94.8 |
| Comparative evaluation example 1-1 | Comparative compound No. 1 | 31.2 | 12.1 |

As apparent from [Table 4], the compounds represented by the above general formulae (I) and (IV) of the present invention exhibited a high absorbance residual rate even after 300 hours of irradiation. On the other hand, the comparative compound was poor in light resistance, as it exhibited a drop in absorbance residual rate after 24 hours of irradiation and a significant drop in absorbance residual rate after 300 hours of irradiation.

Evaluation Examples 2-1 and 2-2

Evaluation of Heat Resistance of Cyanine Compounds Represented by General Formulae (I) and (IV)

Evaluation was made on the heat resistance of the quencher anion salts of the compounds Nos. 1 and 2 obtained in the examples 1 and 2.

Evaluation was made by holding the same test pieces as those used in the above light-resistance test at 100° C. for 100 hours and 400 hours, and thereafter measuring the absorbance residual rate at λmax of the UV absorption spectrum before irradiation. The results are shown in [Table 5].

TABLE 5

| | | Absorbance residual rate (%) | |
|---|---|---|---|
| | Compound | After 100 hours | After 400 hours |
| Evaluation example 2-1 | Quencher anion salt of Compound No. 1 | 90.8 | 75.6 |
| Evaluation example 2-2 | Quencher anion salt of Compound No. 2 | 92.9 | 83.4 |

As seen in [Table 5], the cyanine compounds represented by the above general formulae (I) and (IV) of the present invention and the comparative compound exhibited a high absorbance residual rate even after being held in high temperature for 400 hours.

Evaluation Examples 3-1 and 3-2 and Comparative Evaluation Examples 3-1 and 3-2

The UV spectrum absorption was measured for the optical recording media Nos. 1 and 2 obtained in the examples 6 and 7. The results are shown in [Table 6].

TABLE 6

| | Optical recording medium | λmax (nm) |
|---|---|---|
| Evaluation example 3-1 | Optical recording medium No. 3 | *565.0, 376.0 |
| Evaluation example 3-2 | Optical recording medium No. 2 | *564.0, 378.0 |
| Comparative evaluation example 3-1 | Comparative optical recording medium No. 6 | 371.0 |
| Comparative evaluation example 3-2 | Comparative optical recording medium No. 7 | 657.0 |

*Indicates absorption of quencher anion portion (564.0 nm)

As apparent from [Table 6], the optical recording media each having an optical recording layer made of the optical recording material of the present invention exhibited λmax near 380 to 550 mm in UV spectrum absorption. It was therefore confirmed that both optical recording media allow recording with a laser beam ranging from 380 to 420 nm.

INDUSTRIAL APPLICABILITY

According to the present invention, it is possible to provide novel cyanine compounds having superior absorption wavelength properties and light resistance and being suitable for optical elements. An optical recording material containing such a compound can suitably be used for making an optical recording layer of an optical recording medium.

The invention claimed is:
1. A cyanine compound represented by the following general formula (IV):

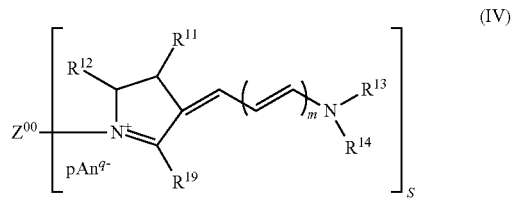

wherein, $R^{11}$ and $R^{12}$ each independently represent a hydrogen atom, a hydroxyl group, a halogen atom, a nitro group, a cyano group, an organic group having 1 to 30 carbon atoms, or a group represented by the following general formula (II), (II'), or (III); $R^{13}$ and $R^{14}$ each independently represent a hydrogen atom, an organic group having 1 to 30 carbon atoms, or a substituent represented by the following general formula (III); $R^{11}$ and $R^{12}$ may be connected together to form a ring structure; $R^{19}$ represents a hydrogen atom or an organic group having 1 to 30 carbon atoms; $R^{13}$ and $R^{14}$ may be connected together to form a heterocycle; m is 0 or 1 to form a monomethine chain or a polymethine chain, respectively, connected to $N(R^{13})R^{14}$; $N-R^{13}$ may be connected together with a methylene group in said monomethine chain or said polymethine chain to form a heterocycle; $Z^{00}$ is an organic group having 1 to 10 carbon atoms; s is 2 to 8; $An^{q-}$ represents an anion having a valence of q; q is 1 or 2; and p represents a coefficient for maintaining charge neutrality;
wherein the general formula (II) and the general formula (II') are:

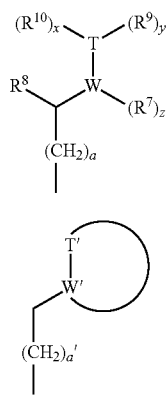

(II)

(II')

wherein in the above general formula (II): a bond between W and T is a double bond, a conjugated double bond, or a triple bond; W represents a carbon atom; T represents a carbon atom or a nitrogen atom; x, y, and z represent 0 or 1; "a" represents a number of 0 to 4; $R^7$ represents a hydrogen atom, a halogen atom, an alkyl group having 1 to 4 carbon atoms that may have a substituent, or an alkoxy group having 1 to 4 carbon atoms that may have a substituent, wherein a methylene group in the alkyl group or the alkoxy group of $R^7$ may be replaced with —O— or —CO—; $R^8$, $R^9$, and $R^{10}$ represent a hydrogen atom, a halogen atom, or an alkyl group having 1 to 4 carbon atoms that may have a substituent, wherein a methylene group in the alkyl group of $R^8$, $R^9$, or $R^{10}$ may be replaced with —O— or —CO—; and $R^8$ and $R^{10}$ may be bonded to form a ring structure; and wherein in the above general formula (II'): a bond between W' and T' is a double bond or a conjugated double bond; W' represents a carbon atom; T' represents a carbon atom or a nitrogen atom; a' represents a number of 0 to 4; a ring containing W' and T' represents a 5-membered ring that may contain a hetero atom, a 6-membered ring that may contain a hetero atom, a naphthalene ring, a quinoline ring, an isoquinoline ring, an anthracene ring, or an anthraquinone ring; and the ring containing W' and T' may be substituted by a halogen atom, a nitro group, a cyano group, an alkyl group, or an alkoxy group; and wherein the general formula (III) is:

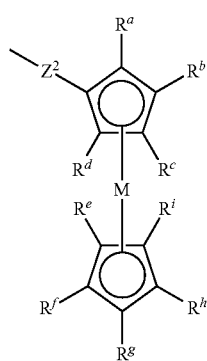

(III)

wherein, $R^a$ to $R^i$ each independently represent a hydrogen atom or an alkyl group having 1 to 4 carbon atoms that may have a substituent, wherein a methylene group in the alkyl group of $R^a$ to $R^i$ may be replaced with —O— or —CO—; $Z^2$ represents a direct bond or an alkylene group having 1 to 10 carbon atoms that may have a substituent, wherein a methylene group in the alkylene group of $Z^2$ may be replaced with —O—, —S—, —CO—, —COO—, —OCO—, —SO$_2$—, —NH—, —CONH—, —NHCO—, —N=CH—, or —CH=CH—; and M represents Fe, Co, Ni, Ti, Cu, Zn, Zr, Cr, Mo, Os, Mn, Ru, Sn, Pd, Rh, Pt, or Ir.

2. A cyanine compound represented by the following general formula (VI):

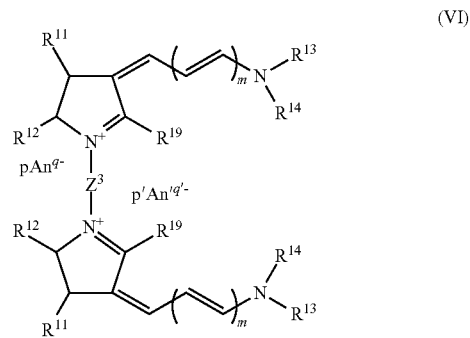

(VI)

wherein, $R^{11}$ and $R^{12}$ each independently represent a hydrogen atom, a hydroxyl group, a halogen atom, a nitro group, a cyano group, an organic group having 1 to 30 carbon atoms, or a group represented by the following general formula (II), (II'), or (III); $R^{13}$ and $R^{14}$ each independently represent a hydrogen atom, an organic group having 1 to 30 carbon atoms, or a substituent represented by the following general formula (III); $R^{11}$ and $R^{12}$ may be connected together to form a ring structure; $R^{19}$ represents a hydrogen atom or an organic group having 1 to 30 carbon atoms; $R^{13}$ and $R^{14}$ may be connected together to form a heterocycle; m is 0 or 1 to form a monomethine chain or a polymethine chain, respectively, connected to N($R^{13}$)$R^{14}$; N—$R^{13}$ may be connected together with a methylene group in said monomethine chain or said polymethine chain to form a heterocycle; $Z^3$ is a direct bond, an alkylene group having 1 to 10 carbon atoms that may have a substituent, or p-dialkylenebenzene, wherein a methylene group in the alkylene group having 1 to 10 carbon atoms or in the p-dialkylenebenzene of $Z^3$ may be replaced with —O—, —S—, —CO—, —COO—, —OCO—, —SO$_2$—, —NH—, —CONH—, —NHCO—, —N=CH—, or —CH=CH—; An$^{q-}$ represents an anion having a valence of q; An'$^{q'-}$ represents an anion having a valence of q'; q and q' each independently are 1 or 2; and p and p' represent a coefficient for maintaining charge neutrality; wherein the general formula (II) and the general formula (II') are:

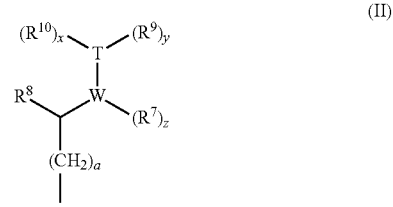

(II)

-continued

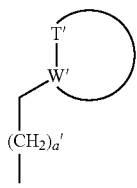
(II')

wherein in the above general formula (II): a bond between W and T is a double bond, a conjugated double bond, or a triple bond; W represents a carbon atom; T represents a carbon atom or a nitrogen atom; x, y, and z represent 0 or 1; "a" represents a number of 0 to 4; $R^7$ represents a hydrogen atom, a halogen atom, an alkyl group having 1 to 4 carbon atoms that may have a substituent, or an alkoxy group having 1 to 4 carbon atoms that may have a substituent, wherein a methylene group in the alkyl group or the alkoxy group of $R^7$ may be replaced with —O— or —CO—; $R^8$, $R^9$, and $R^{10}$ represent a hydrogen atom, a halogen atom, or an alkyl group having 1 to 4 carbon atoms that may have a substituent, wherein a methylene group in the alkyl group of $R^8$, $R^9$, or $R^{10}$ may be replaced with —O— or —CO—; and $R^8$ and $R^{10}$ may be bonded to form a ring structure; and wherein in the above general formula (II'): a bond between W' and T' is a double bond or a conjugated double bond; W' represents a carbon atom; T' represents a carbon atom or a nitrogen atom; a' represents a number of 0 to 4; a ring containing W' and T' represents a 5-membered ring that may contain a hetero atom, a 6-membered ring that may contain a hetero atom, a naphthalene ring, a quinoline ring, an isoquinoline ring, an anthracene ring, or an anthraquinone ring; and the ring containing W' and T' may be substituted by a halogen atom, a nitro group, a cyano group, an alkyl group, or an alkoxy group; and wherein the general formula (III) is:

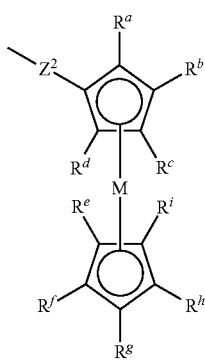
(III)

wherein, $R^a$ to $R^i$ each independently represent a hydrogen atom or an alkyl group having 1 to 4 carbon atoms that may have a substituent, wherein a methylene group in the alkyl group of $R^a$ to $R^i$ may be replaced with —O— or —CO—; $Z^2$ represents a direct bond or an alkylene group having 1 to 10 carbon atoms that may have a substituent, wherein a methylene group in the alkylene group of $Z^2$ may be replaced with —O—, —S—, —CO—, —COO—, —OCO—, —SO$_2$—, —NH—, —CONH—, —NHCO—, —N=CH—, or —CH=CH—; and M represents Fe, Co, Ni, Ti, Cu, Zn, Zr, Cr, Mo, Os, Mn, Ru, Sn, Pd, Rh, Pt, or Ir.

3. A cyanine compound represented by the following general formula (VIII):

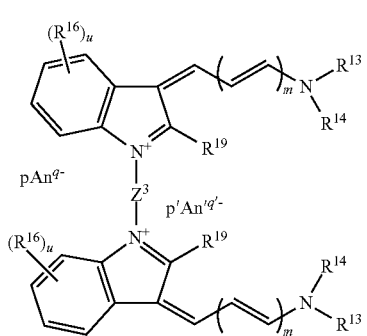
(VIII)

wherein, $R^{16}$ represents a hydrogen atom, an organic group having 1 to 30 carbon atoms, a nitro group, an amino group, a halogen atom, a cyano group, or a heterocycle group having 2 to 20 carbon atoms; u is a number of 1 to 5; $R^{13}$ and $R^{14}$ each independently represent a hydrogen atom, an organic group having 1 to 30 carbon atoms, or a substituent represented by the following general formula (III); $R^{19}$ represents a hydrogen atom or an organic group having 1 to 30 carbon atoms; $R^{13}$ and $R^{14}$ may be connected together to form a heterocycle; m is 0 or 1 to form a monomethine chain or a polymethine chain, respectively, connected to $N(R^{13})R^{14}$; N—$R^{13}$ may be connected together with a methylene group in said monomethine chain or said polymethine chain to form a heterocycle; $Z^3$ is a direct bond, an alkylene group having 1 to 10 carbon atoms that may have a substituent, or p-dialkylenebenzene, wherein a methylene group in the alkylene group having 1 to 10 carbon atoms or in the p-dialkylenebenzene of $Z^3$ may be replaced with —O—, —S—, —CO—, —COO—, —OCO—, —SO$_2$—, —NH—, —CONH—, —NHCO—, —N=CH—, or —CH=CH—; An$^{q-}$ represents an anion having a valence of q; An'$^{q'-}$ represents an anion having a valence of q'; q and q' each independently are 1 or 2; and p and p' represent a coefficient for maintaining charge neutrality; and wherein the general formula (III) is:

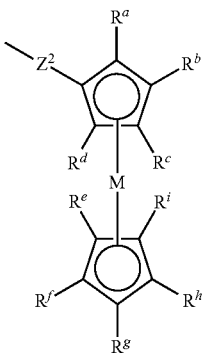
(III)

wherein, $R^a$ to $R^i$ each independently represent a hydrogen atom or an alkyl group having 1 to 4 carbon atoms that may have a substituent, wherein a methylene group in the alkyl group of $R^a$ to $R^i$ may be replaced with —O— or —CO—; $Z^2$ represents a direct bond or an alkylene group having 1 to 10 carbon atoms that may have a substituent, wherein a methylene group in the alkylene group of $Z^2$ may be replaced with —O—, —S—, —CO—, —COO—, —OCO—, —SO$_2$—, —NH—, —CONH—, —NHCO—, —N=CH—, or —CH=CH—; and M represents Fe, Co, Ni, Ti, Cu, Zn, Zr, Cr, Mo, Os, Mn, Ru, Sn, Pd, Rh, Pt, or Ir.

4. An optical recording material comprising at least one cyanine compound according to claim 1.

5. An optical recording medium comprising, on a substrate, an optical recording layer made of the optical recording material according to claim 4.

6. An optical recording material comprising at least one cyanine compound according to claim 2.

7. An optical recording material comprising at least one cyanine compound according to claim 3.

8. An optical recording medium comprising, on a substrate, an optical recording layer made of the optical recording material according to claim 6.

9. An optical recording medium comprising, on a substrate, an optical recording layer made of the optical recording material according to claim 7.

* * * * *